United States Patent
Tamai et al.

(10) Patent No.: US 6,313,214 B1
(45) Date of Patent: Nov. 6, 2001

(54) MELANIN INHIBITING AND CELL GROWTH ACTIVATING COMPOSITIONS CONTAINING COMPOUNDS HAVING LABDANE STRUCTURE

(75) Inventors: Eiko Tamai; Katsuyoshi Tsuchiya; Yoichiro Nishizawa; Minoru Hanada; Kazuhiko Tokoro, all of Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/294,875

(22) Filed: Apr. 20, 1999

(30) Foreign Application Priority Data

Apr. 20, 1998 (JP) .................................. 10-144954

(51) Int. Cl.⁷ .......................... A61K 31/215; A61K 31/19
(52) U.S. Cl. ............................. 524/529; 514/569
(58) Field of Search ............................. 424/450, 63, 401; 514/455, 880, 529

(56) References Cited

U.S. PATENT DOCUMENTS

| | | | |
|---|---|---|---|
| 5,384,126 | * | 1/1995 | Bonte et al. .......................... 424/450 |
| 5,891,464 | * | 4/1999 | Bonte et al. .......................... 424/450 |

FOREIGN PATENT DOCUMENTS

| | | | |
|---|---|---|---|
| 217372 | * | 4/1987 | (EP) ............................. C07D/311/92 |
| 243646 | * | 4/1987 | (EP) ............................. C07D/311/22 |
| 252482 | * | 1/1998 | (EP) ............................. C07D/311/92 |
| 2372822 | * | 3/1977 | (FR) ............................. C07D/311/02 |
| 07-206654 A | | 8/1995 | (JP) . |

OTHER PUBLICATIONS

Gournelis et al., Resin of Eperua ... Ann. Pharm. Fr., vol. 43/6, pp. 565–572. (1986).*
Moll et al., A Calorimetric Bioassay ..., Bol. Soc. Chil. Quim., vol. 43/1, pp. 081–085. (1998).*

* cited by examiner

Primary Examiner—William R. A. Jarvis
Assistant Examiner—Vickie Kim
(74) Attorney, Agent, or Firm—Kubovcik & Kubovcik

(57) ABSTRACT

The present invention provides compounds which have, particularly, an inhibitory activity on production of melanin, a cell activating activity and an anti-bacterial activity, are derived from natural sources, and are safe and not harmful. One or more compounds represented by the following general formula are contained:

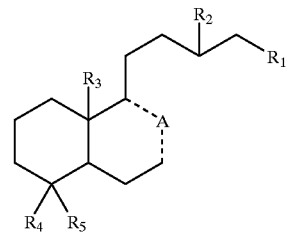

wherein $R^1$ represents —$CH_2OH$, —$COOR^6$ or —COOX, whereupon X is a group capable forming a salt and $R^6$ represents hydrogen or a $C_1$ to $C_3$ lower alkyl group; $R^2$ to $R^5$ each represent hydrogen or a methyl group; and ... A ... represents =$C(CH_3)$—, —$C(CH_3)$=, —$C(=CH_2)$—, —$CH(CH_3)$— or —$C(OH)(CH_3)$—.

6 Claims, No Drawings

MELANIN INHIBITING AND CELL GROWTH ACTIVATING COMPOSITIONS CONTAINING COMPOUNDS HAVING LABDANE STRUCTURE

BACKGROUND OF THE INVENTION

1. Field of the Invention

The present invention relates to a biologically active substance consisting of specific compounds. Further, the present invention relates to a melanin production inhibitor, cell growth activator, anti-bacterial agent, etc. containing the above-mentioned compounds. Further, the present invention relates to an agent for external application onto the skin, oral cavity compositions, bath additives, etc.

2. Prior Art

Compounds with a wide variety of biological activities have been developed heretofore. In particular there are a large number of reports on compounds derived from natural materials especially from the safety point of view.

As typical compounds having biological activity, those having an inhibitory effect on production of melanin are described hereinafter.

As age advances, stains, freckles or deposition of pigment after sunburn tends to be formed, increased or settled into the skin. This is problematic particularly for the middle-aged and the elderly.

Although there are still unrevealed aspects of the mechanism of generation of such acquired pigment (melanin) deposition, it is believed that melanin pigment formation is caused by hormone abnormality and external stimuli such as ultra violet rays from sunlight, oxygen and chemical substances etc., and abnormally deposited in the skin. The development of compounds preventing the formation and deposition of this melanin is highly desired and many compounds have been developed therefor. These compounds include ascorbic acid and derivatives thereof, a placenta extract, hydroquinone, kojic acid, arbutin and ellagic acid, and further there are a large number of reports on melanin production-inhibiting components extracted from plants, and these include a chamomile extract (*Matricaria chamomilla* L. (Composite)) disclosed in Japanese Patent Application Laid-Open No. 8-92056, a golden flower root extract (*Scutellaria baicalensis* G. (Labiatae)) disclosed in Japanese Patent Application Laid-Open No. 8-104616, a cumin seed (*Cuminum cyminum* L. (Umbelliferae)) disclosed in Japanese Patent Application Laid-Open NO. 8-119848 and a wolo extract (*Borassus flabellifera* (Palmac)) disclosed in Japanese Patent Application Laid-Open No. 10-29928.

Further, the present inventors also found that a fraction obtained by purifying solvent extracts from various plants by silica gel chromatography strongly inhibits the production of melanin in B16 melanoma cells, and filed for a patent (Japanese Patent Application No. 9-254025, Aug. 15, 1997). As a substance having a labdan structure, manool, an extract of *Dacrydium biforme* is reported to have an inhibitory effect on production of melanin (Japanese Patent Application Laid-Open No. 6-72855). Further the inhibitory effect of derivatives thereof on melanin production is also reported (Japanese Patent Application Laid-Open Nos. 7-25754, 7-69858, 7-206625 etc.).

However, the majority of these conventional melanin production inhibitors are inadequate with respect to stability, effects, adverse side effects, etc., so a new melanin inhibitor has been desired.

Cell growth activators are now described hereinafter. In aged skin, the activity of skin cells is weakened so that wrinkles and flabby skin are formed. Recently, there are many studies in which skin cells themselves are activated and the function of the skin itself in thus activated to improve skin conditions, and attention has been paid to the development of cell growth activators for activating weakened cells as well as to the incorporation of such cell activators into an agent for external application onto the skin. Conventional materials used for imparting cell-activating activity include alpha-hydroxy acids such as glycolic acids, single-component materials such as hormones, vitamins, photosensitive elements, allantoin, etc., and extracted components including animal and plant extracts such as placenta extract, lactobacillus extract, shikon extracts, aloe extract, carrot extract, etc. Further, the present inventors also found that there is strong cell-activating activity in distilled residues of solvent extracts, etc. from various plants, and filed for a patent (Japanese Patent Application Laid-Open No. 8-284572, Oct. 8, 1996). Further, labdanum furanoid diterpenoids (WO 97/45099) are reported as cell differentiation-inducing materials having a labdan structure. However, the majority conventional materials and extracts having cell-activating activity are unsatisfactory with respect to their effects, so that they have to be applied in a large amount. Also their stability in stage is not satisfactory. Moreover, they may create safety problems because of their stimulating properties or similar nature.

Anti-bacterial agents are now described hereinafter. A large number of microorganisms are present on the skin and many of them are not problematic to a healthy skin, but under bad skin conditions or bad general conditions, these microorganisms invade hair follicles, sweat glands and damaged sites to act as causative agents for infections.

In addition, there are some microorganisms which cause body odors or dandruff or oxidize secreted lipids to exert adverse effects an causative factors for acne. To kill such microorganisms, many compounds have been used, but many of them are chemically synthesized products, so there has been a demand for highly safe anti-bacterial agents derived from natural sources.

The anti-bacterial activity of Cistus absolute as one of the extracts from *Cistus ladaniferus* L., *Cistus creticus* L., *Cistus monoperiensis* L., *Cistus salvifolius*, etc. has already been reported (Nippon Keshohin Gijyutusha Kaishi, 27, 227 (1993)), but its active ingredient is not referred to therein.

SUMMARY OF THE INVENTION

The object of the present invention is to provide compounds which have a wide variety of biological activities, are derived from natural sources, and are safe and user-friendly. In particular, the object of the present invention is to provide compounds having an inhibitory activity on production of melanin, a cell-activating activity and an anti-bacterial activity.

As a result of their eager study to solve this problem, the present inventors found that extracts with hot water, or extracts with ethanol, hexane, etc. of stems, branches, leaves, etc. of *Cistus ladaniferus* L., *Cistus creticus* L., *Cistus monoperiensis* L., *Cistus salvifolius*, etc. have a strong inhibitory activity on production of melanin, a cell-activating activity and an anti-bacterial activity, that these actions are based on labdanolic acid, and further that labd-7-en-15-oic acid, labd-8(17)-en-15-oic acid, and labd-8-en-15-oic acid obtained by molecular distillation of the above extracts, or of labdanolic acid have a strong inhibitory activity on production of melanin, a cell-activating activity and an anti-bacterial activity. Further, the present inventors found that salts thereof or methyl and ethyl ester derivatives thereof and reduced derivatives thereof have also the same activity, and as a result of additional examination, the present invention was completed at last. The biologically active substance of the present invention is one or more compounds represented by the following general formula (1):

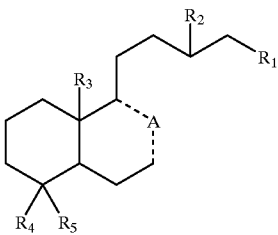

wherein $R^1$ represents —$CH_2OH$, —$COOR^6$, or —COOX, where X is a group capable forming a salt and $R^6$ represents hydrogen or a $C_1$ to $C_3$ lower alkyl group; $R^2$ to $R^5$ each represent hydrogen or a methyl group; and . . . A . . . represents =C($CH_3$)—, —C($CH_3$)=, —C(=$CH_2$)—, —CH($CH_3$)— or —C(OH)($CH_3$)—.

In the formula, X includes a group capable of forming a salt such as sodium, potassium, ammonium, etc., and $R^6$ includes hydrogen, a methyl group, an ethyl group and a propyl group.

In the present invention, the biologically active substance refers to a substance having one or more activities selected from an inhibitory activity on melanin production, a cell-activating activity and an anti-bacterial activity.

DETAILED DESCRIPTION OF THE INVENTION

The above compounds are those known in the art and their processes are also known. For example, labdanolic acid is a component in labdanum gum extracted from *Cistus ladaniferus* (J. Chem. Soc., 1956, 4259–4262), and labd-8(17)-en-15-oic acid (eperuic acid) and labd-8-en-15-oic acid are obtained by chemically treating labdanolic acid (J. Chem. Soc., 1956, 4262–4271). Further, it is reported that eperuic acid is a component in a resin derived from an *Eperua falcata* tree of the Leguminosae (J. Chem. Soc., 1955, 658–662), and labd-7-en-15-oic acid (cativic acid) is a component in a resin from *Prioria copaifera* G. tree of the Leguminosae (J. Am. Chem. Soc., Vol. 79, 1201–1205, 1957).

However, it was not known which biological activity these substances possess, neither was it known that they possess an inhibitory activity on production of melanin, a cell-activating activity and an anti-bacterial activity.

Although the plants used for preparing the compounds defined in the present invention are not particularly limited insofar as they are plant containing said compounds, it is particularly advantageous to employ *Cistus ladaniferus* L., *Cistus creticus* L., *Cistus monoperiensis* L., and *Cistus salvifolius* plants (Cistaceae family). These are used alone or in combinations thereof. The site of plant used is not particularly limited, and use is made of leaves, branches, stems, barks, etc. These may be used just after being harvested or after being dried.

Preferably, the method of extracting the desired compounds from said plants makes use of one or more solvents selected from the group consisting of water, lower alcohols, petroleum ether and hydrocarbons. The lower alcohols are those containing 1 to 4 carbon atoms, preferably methanol, ethanol, etc.

The petroleum ether used may be not only the one known in the art but also a commercial product.

The hydrocarbon solvents are aliphatic hydrocarbons, alicyclic hydrocarbons and aromatic hydrocarbons which are liquid at ordinary temperatures and, preferably, aliphatic hydrocarbons and aromatic hydrocarbons which are liquid at ordinary temperatures, among which hydrocarbons such as hexane and toluene are particularly preferable.

Although the operation of extraction differs depending on the plant and solvent used, usually divided pieces of the plant are immersed in the solvent, optionally under gentle stirring, at room temperature to a temperature of 50° C.

Further, a soxhlet extractor known in the art may also be used.

The time required for extraction is usually 3 to 48 hours.

Alternatively, a method of steam distillation or boiling in hot water after leaves, branches or stems of the plant are disrupted may also be adopted in the present invention. In this case, gum which floats on water upon steam distillation or hot-water extraction is removed and then separated from insolubles by means of solvent extraction.

Further, commercially available products obtained from the above plants by any of the methods described above may be used.

The crude extract thus obtained contains 25 to 35% labdanolic acid. This crude extract itself may be used as a melanin production inhibitor, cell activator and anti-bacterial agent.

Hereinafter, a typical method of obtaining the acid or a mixture of the acids from the crude extract or from a commercially available extract is described, but the present invention is not limited to this example.

The above crude extract or a commercially available extract is subjected to molecular distillation under reduced pressure at 0.1 to 0.5 mm Hg whereby a fraction at 160 to 230° C. and, preferably, 180 to 220° C. is collected. This fraction contains a mixture of labd-7-en-15-oic acid, labd-8(17)-en-15-oic acid and labd-8-en-15-oic acid.

As the melanin production inhibitor, cell activator and anti-bacterial agent, this acid mixture may be used as such or if necessary as salts or methyl or ethyl ester derivatives thereof.

Then, the three acids are separated from this acid mixture.

Specifically, this acid mixture is dissolved in ethanol, then reacted to form ethyl ester derivatives in the presence of a catalytic amount of sulfuric acid, and subjected to silica gel chromatography on silica gel treated with silver nitrate. The column is washed with hexane and then the ethyl ester is eluted with 1% ethyl acetate-hexane. First, labd-8 -en-15-oic acid ethyl ester is eluted and then labd-7-en-15-oic acid ethyl ester and labd-8(17)-en-15-oic acid ethyl ester are eluted in this order. The solvent is distilled off whereby purified products of the respective ethyl ester derivatives are obtained. Each of the ethyl ester derivatives thus obtained is hydrolyzed to give a free acid, and the free acid is further reacted with diazomethane to give its methyl ester derivative.

The resulting acids, methyl esters, ethyl esters or mixtures thereof are useful as melanin production inhibitors, cell activators, and anti-bacterial agents.

Further, these can be incorporated into an agent for external application onto the skin, a bath additive, an oral cavity composition, etc. to give a corresponding agent having an inhibitory activity on production of melanin, a cell-activating activity and an anti-bacterial activity. Further, the compound (1) of the present invention can be added to prepare an anti-aging agent and anti-wrinkle agent, etc.

The amount of said melanin production inhibitor, cell activator and anti-bacterial agent incorporated is 0.01 to 10% by weight, preferably 0.05 to 5% by weight, for the agent for external application onto the skin, 0.1 to 10% by weight, preferably 0.2 to 5% by weight, for the bath additives, 0.1 to 10% by weight, preferably 0.2 to 5% by weight, for an oral cavity composition, and 0.01 to 5% by weight, preferably 0.05 to 2% by weight, for an anti-bacterial agent.

The amount of the compound (1), if incorporated into face lotion, milky lotion, cream, etc., is usually 0.05 to 10% by weight, preferably 0.05 to 2% by weight.

The method of incorporation of the compound (1) into a melanin production inhibitor, a cell activator, an anti-bacterial agent, etc. is not particularly limited. For example, the compound(s) of the invention may be incorporated after being diluted with a usual organic solvent used in perfumes, that is, ethylene glycol, propylene glycol and lower alcohols which are used alone or as a mixture thereof, or after being diluted with a mixture of such solvent and a surface active agent, or after being mixed with conventional perfume materials. Alternatively, it may be incorporated as such in the absence of other materials.

Further, the melanin production inhibitor, cell activator, anti-bacterial agent, etc. of the present invention can contain not only the above essential ingredients but also other ingredients used in agents for external application onto the skin, such as usual cosmetics, quasi drug preparations, pharmaceutical preparations, etc. For example, it is possible to incorporate skin whitening agents, cell activators, humectants, antioxidants, oil components, surface active agents, thickeners, inorganic fillers, coloring agents, pH adjusters, preservatives, perfumes, UV absorbers, various skin nutrients, etc., depending on the object or on necessity.

Hereinafter, some of these ingredients are exemplified. As the skin whitening agents, mention can be made of arbutin, kojic acid, ellagic acid, ascorbic acid, etc. and various derivatives thereof, as well as extracts from various animals and plants such as placenta extract, etc. As the cell activators, mention is made of alpha-hydroxy acids such as glycolic acid, etc., hormones, vitamins, various animal and plant extracts. The humectant includes sorbitol, xylitol, glycerin, propylene glycol, sodium pyrrolidonecarboxylate, lactic acid, hyaluronic acid, collagen etc.; the antioxidants include vitamin E, butylhydroxytoluene, butylhydroxyanisol etc.; the oil components include vegetable fats and oils such as liquid paraffin, paraffin, olive oil, coconut oil, etc. and animal fats and oils such as tallow, porcine fat, mink oil, squalane, etc., and synthetic oils such as methyl polysiloxane, silicone oil, glyceryl triisopalmitate, etc.

The surface active agents include anionic surface active agents such as sodium lauryl sulfate, triethanolamine laurate, etc., cationic surface active agents such as cetyl trimethyl ammonium chloride, bonzalkonium chloride, etc., nonionic surface active agents such an glyceryl monooleate, sorbitan monostearate, polyoxyethylene hydrogenated castor oil, and sucrose fatty acid ester; the thickeners include carboxymethylcellulose, hydroxyethylcellulose, carboxy-vinylpolymers, sodium alginate carrageenan, etc.; the inorganic fillers include talc, sericite, mica, kaolin, zinc white, titanium oxide, magnesium oxide, etc.; the pH adjusters include organic acids, such as citric acid, sodium citrate, etc. and salts thereof; the preservatives include urea, parabens such as methyl paraben, ethyl paraben, etc., sodium benzoate, ethyl alcohol, etc. Further, by adding various UV absorbers, it is also possible to improve the effect of preventing sunburns.

EXAMPLES

Hereinafter, the present invention is described in more detail by reference to the Examples, which are not intended to limit the present invention.

Example 1

A commercial labdanum absolute (Givaudan Co., Ltd.) was subjected to molecular distillation. The labdanum absolute (10 g) was subjected to molecular distillation under reduced pressure (0.1 mm hg) to collect a fraction (4.3 g) at 180 to 220° C. This fraction contains a mixture of labd-8-en-15-oic acid (Compound 1), labd-7-en-15-oic acid (compound 4) and labd-8(17)-en-15-oic acid (Compound 7) (this mixture is referred to hereinafter as the acid mixture).

The acid mixture (1 g) was dissolved in ether (2 ml) and diazomethane was added dropwise thereto to give methyl ester derivatives (0.96 g) (the methyl esters are referred to hereinafter as the methyl ester mixture).

Similarly, this acid mixture (10 g) was dissolved in ethanol (100 ml) and esterified in the presence of a sulfuric acid catalyst to give ethyl ester derivatives (9.5 g) (the ethyl ester derivatives are referred to hereinafter as the ethyl ester mixture).

Example 2

For separation of these three acids, the ethyl ester mixture was subjected to silica gel chromatography. The ethyl ester mixture (10 g) was dissolved in hexane (100 ml) and applied to a column packed with silica gel treated with silver nitrate and then eluted with a solvent. The eluting solvent firstly used was hexane and then a mixed solvent of hexane containing 1% by volume of ethyl acetate. Labd-8-en-15-oic acid ethyl ester was first eluted, and then labd-7-en-15-oic acid (cativic acid) ethyl ester and labd-8(17)-en-15-oic acid (eperuic acid) ethyl ester were eluted in this order. The eluate containing each of the components was collected and the solvent was distilled off, whereby purified products of the respective ethyl ester derivatives (0.83 g, 0.16 g and 0.63 g in the order of elution) were obtained. Each of the ethyl ester derivatives thus obtained was hydrolyzed to give free acids.

Further, diazomethane was added dropwise to the free acid, and the solvent was distilled off whereby the methyl ester derivatives were obtained.

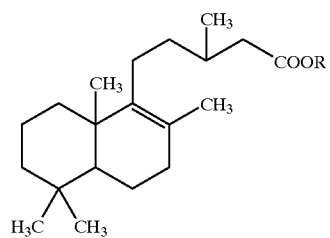

Compound (1): R=H (labd-8-en-15-oic acid)
Compound (2): R=CH₃
Compound (3): R=C₂H₅

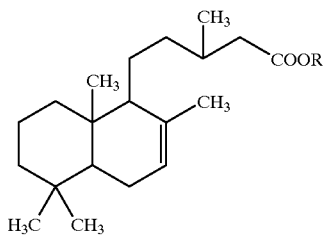

Compound (4): R=H (labd-7-en-15-oic acid)
Compound (5): R=CH₃
Compound (6): R=C₂H₅

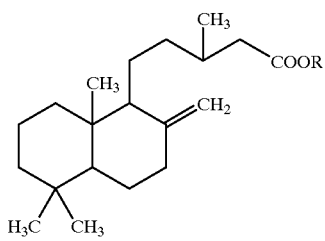

Compound (7): R=H (labd-8(17)-en-15-oic acid)
Compound (8): R=CH₃
Compound (9): R=C₂H₅

Example 3

The ethyl ester mixture (4.3 g) obtained in Example 1 was dissolved in ethanol (10 ml), and 5% palladium carbon catalyst (0.2 g) was added thereto for hydrogenation reactions to give compound 11 (4.1 g). Further, it was hydrolyzed to give compound 10.

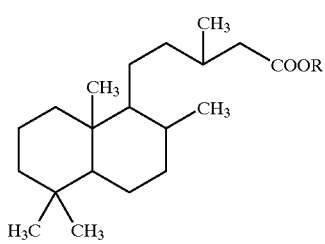

Compound (10): R=H (labden-15-oic acid)
Compound (11): R=C₂H₅

Example 4

The ethyl ester mixture (3.2 g) obtained in Example 1 was dissolved in tetrahydrofuran (10 ml) and to this solution a solution of lithium aluminum hydride (0.21 g) in tetrahydrofuran (10 ml) was added dropwise at room temperature to give an alcohol derivative mixture (2.32 g), i.e., the terminus —COOH group of labd-8-en-15-oic acid (Compound 1), labd-7-en-15-oic acid (Compound 4) and labd-8(17)-en-15-oic acid (Compound 7) was replaced with —CH₂OH group. This alcohol derivative mixture may be used directly as a melanin production inhibitor, a cell activator and an anti-bacterial agent.

Test Example 1
Melanin Formation Prevention Test

B16 melanoma cells were suspended (10,000 cells/ml) in DMEM (Dulbecco's modified eagle medium) containing 10% FBS (fetal bovine serum) and 8 ml of the suspension was added to a cell culture bottle with a 25 cm² bottom surface area, and cultured at 37° C. in the presence of 5% carbon dioxide for 3 days. After 3 days of culture, the old medium was exchanged with 8 ml of fresh medium. 40 micro-liters of a sample solution, in which compounds of the present invention had been dissolved in ethanol to give a final concentration shown in the table, were further added thereto. As the control, ethanol only was added. After the medium change, the cells were further cultured for 3 days under the same conditions. After culture was finished, the medium was removed, and the cells were recovered by treatment with trypsin (DIFCO) and suspended in 4 ml of phosphate buffered saline (PBS) and a predetermined amount (1/40) of this suspension was used to measure the number of cells in a Coultar counter (Sysmex Co.) to determine the degree of cell proliferation.

The degree of cell proliferation was determined according to the following equations:

Degree of cell proliferation (%)=(number of cells in sample)/(number of cells in control)×100

The remainder of the cell suspension was centrifuged and then washed with 5% trichloroacetic acid, then with ethanol/ethyl ether (3:1 by volume), and with ethyl ether and the cells were dried, and 2N—NaOH was added thereto to dissolve (melanin in) the cells under heating at 70° C. and measured for its optical density (OD) at 420 nm. Using a calibration curve of synthetic melanin, the amount of melanin/million cells was determined from the OD and the degree of inhibition of melanin production was determined according to the following equation:

Degree of inhibition of melanin (%)=(amount of melanin in control−amount of melanin in sample)/(amount of melanin in control)×100

A degree of inhibition of melanin of 60% or more and a degree of cell proliferation of 70% or more are indicative of superior safety and superior inhibitory activity on production of melanin, so that highly practical usage can be envisaged.

TABLE 1

Degree of Inhibition of Melanin Production

| Sample | Concentration (ppm) | Degree of melanin inhibition | Degree of cell proliferation |
| --- | --- | --- | --- |
| Crude extract | 6.3 | 75% | 110% |
| Acid mixture | 6.3 | 77% | 143% |
| Methyl ester mixture | 6.3 | 80% | 122% |
| Ethyl ester mixture | 6.3 | 75% | 122% |
| Compound 1 | 3.1 | 80% | 109% |
| Compound 3 | 6.3 | 74% | 115% |
| Compound 4 | 6.3 | 87% | 109% |
| Compound 6 | 6.3 | 74% | 109% |
| Compound 7 | 6.3 | 79% | 111% |
| Compound 9 | 6.3 | 61% | 103% |
| Compound 10 | 6.3 | 83% | 97% |
| Compound 11 | 6.3 | 75% | 107% |
| Kojic acid | 200.00 | 34% | 94% |
| Arbutin | 6.3 | 74% | 100% |
| Ellagic acid | 3.1 | 68% | 98% |

Test Example 2
Combination Test with Existing Tyrosinase Inhibitors

Using the method of Test Example 1, arbutin, kojic acid, and ellagic acid, which were known to have an inhibitory activity on tyrosinase, were mixed with the compound of the present invention and examined for the degree of inhibition of melanin production in B16 melanoma cells as well as for the degree of proliferation of the cells, to determine the effect of their combined use.

TABLE 2

Effect of Combined use with arbutin

| Sample | Concentration (ppm) | Degree of melanin inhibition | Degree of cell proliferation |
|---|---|---|---|
| Acid mixture (A) | 0.4 | 9% | 103% |
| Compound 1 | 0.4 | 22% | 115% |
| Compound 4 | 0.4 | 28% | 115% |
| Arbutin (E) | 0.8 | 22% | 89% |
| (A) + (E) | 0.4 + 0.8 | 52% | 128% |
| (B) + (E) | 0.4 + 0.8 | 54% | 132% |
| (C) + (E) | 0.4 + 0.8 | 56% | 127% |

TABLE 3

Effect of combined use with kojic acid

| Sample | Concentration (ppm) | Degree of melanin inhibition | Degree of cell proliferation |
|---|---|---|---|
| Acid mixture (A) | 0.4 | 37% | 114% |
| Compound 1 (B) | 0.4 | 46% | 122% |
| Compound 4 (C) | 0.4 | 51% | 119% |
| Compound 7 (D) | 0.4 | 34% | 130% |
| Kojic Acid (E) | 200 | 34% | 94% |
| (A) + (E) | 0.4 + 200 | 55% | 96% |
| (B) + (E) | 0.4 + 200 | 43% | 96% |
| (C) + (E) | 0.4 + 200 | 71% | 96% |
| (D) + (E) | 0.4 + 200 | 54% | 113% |

TABLE 4

Effect of combined use with ellagic acid

| Sample | Concentration (ppm) | Degree of melanin inhibition | Degree of cell proliferation |
|---|---|---|---|
| Acid mixture (A) | 0.4 | 17% | 106% |
| Compound 7 (B) | 0.4 | 30% | 111% |
| Ellagic Acid (C) | 1.6 | 17% | 98% |
| (A) + (C) | 0.4 + 1.6 | 31% | 111% |
| (B) + (C) | 0.4 + 1.6 | 31% | 100% |

As can be seen from Tables 2, 3 and 4, when arbutin, kojic acid, and ellagic acid were used with the compound of the present invention, they showed higher inhibitory activity on melanin production than when they were used alone. The degree of cell proliferation was also higher than when these tyrosinase inhibitors were used alone. This indicates that these materials used in combination with the compounds of the present invention bring about a higher effect as skin whitening agents.

Test Example 3
Effect of Diminishing UV Ray-induced Pigment Stains in Guinea Pigs Hair was carefully removed from the back of 5 brown guinea pigs, and a shielding plate provided with four 2.5 cm×2.5 cm openings was attached to the portion from which hair had been removed, followed by irradiating it 3 times every second day with UVB rays at an intensity of 450 mj/cm$^2$. Immediately after the irradiation of UVB rays, a 70 micro-liters sample was applied onto the irradiated site once per day for 35 days, and the amount of pigment diminished by this treatment was examined on the days shown in Table 5. The sample used was an ethanol solution containing 1% acid mixture obtained in Example 4 as the compound of the invention, and ethanol only was applied as the control.

For evaluation of the activity, each application site was measured by a colorimeter (CR200b, Minolta Co Ltd.). $\Delta Lx$ is the difference between the L value after the sample application (value changing with time) and the L value of the portion before the sample application started, and then $\Delta \Delta L$ value was determined by subtracting $\Delta Lo$ value (i.e. the value similarly determined for the portion to which ethanol was applied) from the $\Delta Lx$ value. The $\Delta \Delta L$ value can be determined according to the equation:

$$\Delta\Delta L = (Lo - Lx) - (L'o - L'x)$$

Lo: L value of the test site (site to which the sample was applied) before sample application Lx: L value of the test site (site to which the sample was applied) on Day x after sample application L'o: L value of the control site (site to which ethanol was applied) before ethanol application L'x: L value of the control site (site to which ethanol was applied) on Day x after ethanol application The same experiment was conducted using an ethanol solution containing 7% kojic acid. The results are shown in Table 5.

TABLE 5

Change in $\Delta\Delta L$ value

| | | $\Delta\Delta L$ | | |
|---|---|---|---|---|
| Sample | Concentration | Day 14 | Day 28 | Day 35 |
| Acid Mixture | 1% | 0.30 | 2.25 | 2.15 |
| Kojic Acid | 7% | 1.32 | 1.52 | 1.40 |

As can be seen from Table 5, the acid mixture as one of the compounds of the present invention has an evident action of diminishing pigment stains as compared with the control. The activity was stronger than that of kojic acid after Day 28. When observed with the passage of time, kojic acid was found to indicate the activity at an earlier stage until Day 14.

Test Example 4
Mushroom Tyrosinase Inhibition Test

Commercial mushroom-derived tyrosinase (Sigma) was used to examine inhibitory activity on tyrosinase. 0.2 ml sample solution was added to 2.3 ml phosphate buffer so as to give a final concentration shown in Table 6, then 0.1 ml of a tyrosinase solution (1000 U/ml) was added thereto, and further 0.4 ml of L-tyrosine solution (0.3 mg/ml) was added thereto as the substrate, and the mixture was kept at 37° C. for 30 minutes. After reaction, the absorbance (OD) at a wavelength of 490 nm was measured and the degree of inhibition of tyrosinase reaction was determined according to the following equation. For comparison, arbutin and kojic acid known as tyrosinase inhibitors were also examined.

Degree of inhibition (%)=(1−((sample OD-blank OD)/(Sample-free OD-blank OD)))×100

Sample: The buffer, the enzyme solution, the substrate solution and the sample solution Sample-free: The buffer, the enzyme solution and the substrate solution Blank: The buffer and the enzyme solution

TABLE 6

Degree of inhibition of mushroom tyrosinase

| Sample | Concentration (ppm) | Degree of inhibition |
|---|---|---|
| Acid mixture | 25 | 0% |
| Compound 1 | 25 | 0% |
| Compound 4 | 25 | 0% |
| Compound 7 | 25 | 0% |
| Arbutin | 100 | 29% |
| Kojic Acid | 25 | 67% |

As shown in Table 6, arbutin and kojic acid known as tyrosinase inhibitors inhibited mushroom tyrosinase, while the compounds of the present invention as the melanin production inhibitor did not show any inhibitory activity, thus suggesting the possibility that their activity does not lie in the inhibition of tyrosinase.

Test Example 5
Test of Tyrosinase Inhibition in B16 Melanoma Cells

B16 melanoma cells were cultured for 3 days in DMEM containing 10% FBS at 37° C. in the presence of 5% carbon dioxide. The cells proliferated after culture were recovered by treatment with trypsin, then suspended in PBS containing 0.1% Triton X100 at a density of ten million cells/ml and disrupted by sonication. The product obtained was centrifuged at 11,000 G for 20 minutes, and the resulting supernatant was used as a crude enzyme solution. 0.2 ml sample solution was prepared in a phosphate buffer so as to give a final concentration shown in Table 7. Added thereto was 0.2 ml of crude enzyme solution. The mixture was preliminarily kept at 37° C. for 5 minutes, and 0.2 ml L-DOPA solution (0.5 mg/ml) was added as the substrate, and the mixture was kept at 37° C. for 3 hours. After 3 hours, the absorbance (OD) at a wavelength of 490 nm was measured, and the degree of inhibition of tyrosinase was determined according to the equation shown in Test Example 4. For comparisons arbutin and kojic acid known as tyrosinase inhibitors were also examined.

TABLE 7

Degree of inhibition of tyrosinase in B16 melanoma cells

| Sample | Concentration (ppm) | Degree of inhibition |
|---|---|---|
| Acid mixture | 25 | 0% |
| Compound 1 | 25 | 0% |
| Compound 4 | 25 | 0% |
| Compound 7 | 25 | 0% |
| Arbutin | 100 | 35% |
| Kojic Acid | 25 | 62% |

As shown in Table 7, arbutin and kojic acid known as tyrosinase inhibitors inhibited tyrosinase in B16 melanoma cells, while the compounds of the present invention as the melanin production inhibitor did not exhibit any inhibitory activity.

Test Example 6
Test of Cell Activating Activity

Human-derived normal skin fibroblasts (NB1RGB: Institute of Physical and Chemical Research) were suspended into DMEM containing 10% FBS to give a concentration of 20,000 cells/ml, and 5 ml each of this cellular suspension was introduced into each of 25 $cm^2$ bottles, cultured at 37° C. in the presence of 5% carbon dioxide for 24 hours. To each bottle, was added 10 micro-liter (0.2%) of the ethanol solution containing the compound to give the final concentration shown in Table 8. The cells were cultured for an additional 3 days. After 3 days the old medium was discarded and 5 ml fresh medium was added, and the sample was further added thereto. After this exchange of the medium, the cells were further cultured for another 3 days. Then cells were removed with trypsin and the number of cells in each bottle was counted with a Coultar counter.

Simultaneously, as the control, only ethanol was added and the NB1RGB cells were cultured and the number of cells were counted in the same manner.

The number of cells in each bottle to which the sample had been added was determined as a relative value to the number (as 100) of cells in the control after cultured, and the results are shown in Table 8. As the comparative example, glycolic acid known to have cell activating activity was examined and shown in the table.

TABLE 8

Degree of cell proliferation of fibroblasts

| Sample | Concentration (ppm) | Degree of cell proliferation |
|---|---|---|
| Crude extract | 8.0 | 130% |
| Acid mixture | 8.0 | 130% |
| Methyl ester mixture | 4.0 | 126% |
| Ethyl ester mixture | 4.0 | 110% |
| Compound 3 | 8.0 | 134% |
| Compound 6 | 8.0 | 134% |
| Compound 7 | 8.0 | 128% |
| Compound 9 | 8.0 | 127% |
| Compound 10 | 8.0 | 126% |
| Compound 11 | 8.0 | 104% |
| Alcohol derivative mixture | 4.0 | 138% |
| Glycolic acid | 4.0 | 120% |

As shown in Table 8, the compounds of the present invention showed a strong activity of activating proliferation of NB1RGB fibroblasts.

Test Example 7

Anti-bacterial Activity Test

A test was conducted using the 8 aerobic microorganisms and 2 anaerobic microorganisms shown in Table 9 below. The aerobic microorganisms were examined in an agar medium dilution method and the anaerobic microorganisms were examined in a liquid medium dilution method under anaerobic culture conditions.

Agar Medium Dilution Method

Muller Hinton agar medium (DIFCO) was heated and dissolved and 10 ml of the medium was introduced into each test tube, sterilized and used. The sample was prepared by dissolving in ethanol and the resulting ethanol solution was diluted 2-fold serially with ethanol, and 100 micro-liters of sample solution were added to 10 ml of each dissolved agar medium, then stirred, introduced into a Petri dish of 9 cm in diameter, and solidified at room temperature. Each test microorganism in a well grown slant was inoculated via one loop of platinum into 10 ml Muller Hinton broth (DIFCO) and cultured with shaking at 27° C. for 24 hours and used as a microbial fluid. This fluid was diluted at $10^8$ CFU (Colony forming unit)/ml, and 5 micro-liters of the diluted fluid were inoculated onto the agar and cultured at 37° C. overnight. Inoculation of the microorganism was conducted using microplanter MIT-P for 27 tubes test microorganisms (Sakuma Seisakusho K. K.).

Judgement of MIC(minimum inhibitory concentration) was conducted by comparison with the control where the test microorganism was inoculated and grown onto a Muller Hinton agar plate containing 100 micro-liter ethanol, and the concentration at which the microorganism did not grow was regarded as MIC.

Liquid Medium Dilution Method 10 ml GAM broth (Nissui) was introduced into each test tube equipped with a cap and sterilized. 100 micro-liter of the sample solution prepared for agar medium dilution method was added to each test tube and lightly stirred, and 100 micro-liter test microbial solution ($10^7$ CFU/ml) was added thereto, then capped and incubated at 37° C. The test microbial solution was prepared by introducing 100 micro-liter stock microbial solution into 10 ml GAM broth in a test tube then capping the tube and fermenting it at 37° C. overnight.

Judgement of MIC was conducted by comparison with the control to which 100 micro-liter ethanol was added, and the concentration at which the microorganism did not grow was regarded as MIC.

TABLE 9

Test Microorganisms

| Strains | Test Microorganism Code |
|---|---|
| Aerobic microorganisms: | |
| Staphylococcus epidermidis JCM 2414 | Se-1 |
| Staphylococcus epidermidis var. H-6 | Se-2 |
| Corynebacterium minutissimum ATCC 23348 | Cm-1 |
| Corynebacterium xerosis JCM 1324 | Cx-2 |
| Malassezia furfur IFO 0656 | Mf-1 |
| Staphylococcus aureus IFO 12732 | Sa-3 |
| Bacillus subtilis PCI 219 IFO 3134 | Bs-1 |
| Anaerobic Microorganisms: | |
| Propinibadterium Acnes ATCC 12818 | Pa-1 |
| streptococcus mutans JCM 5157 | Su-1 |

TABLE 10

Results of the anti-bacterial test (MIC: ppm)

| Test Mircro- organism code | Sample | | | | |
|---|---|---|---|---|---|
| | Acid Mixture | Compound 1 | Compound 4 | Compound 7 | Compound 10 |
| Se-1 | 12.5 | 6.3 | 12.5 | 6.3 | 6.3 |
| Se-2 | 12.5 | 6.3 | 12.5 | 6.3 | 6.3 |
| Cm-1 | 12.5 | 6.3 | 6.3 | 12.5 | 6.3 |
| Cx-2 | 12.5 | 12.5 | 12.5 | 12.5 | 12.5 |
| Mf-1 | 6.3 | 6.3 | 6.3 | 6.3 | 6.3 |
| Sa-3 | 12.5 | 12.5 | 12.5 | 12.5 | 6.3 |
| Bs-1 | 12.5 | 6.3 | 12.5 | 12.5 | 6.3 |
| Pa-1 | NT | 12.5 | NT | NT | 12.5 |
| Su-1 | NT | 6.3 | NT | NT | 6.3 |

In this table, NT means that the test was not conducted.

As shown in Table 10, the free acids as the compounds of the invention exhibited strong activity toward causative bacteria for body odors (Se-1, Se-2), for dandruff (Mf-1), for acne (Pa-1), for caries (Su-1) etc.

Example 5

The melanin production inhibitor of the present invention was used to prepare face lotion, milky lotion, cream, pack, a bath additive and cream foundation respectively.

(1) Face lotion

TABLE 11

| Ingredients | Incorporation amount (% by weight) |
|---|---|
| Conc. Glycerin | 3.0 |
| 1,3-Butylene glycol | 2.0 |
| Polyoxyethylene sorbitan monolaurate | 1.0 |
| Ethanol | 5.0 |
| Perfume | suitable amount |
| Acid mixture (Example 1) | 1.0 |
| Preservative | suitable amount |
| Purified water | Adjusted to 100% |

(2) Milky lotion

TABLE 12

| Ingredients | Incorporation amount (% by weight) |
|---|---|
| Squalane | 5.0 |
| Vaseline | 2.0 |
| Beeswax | 0.5 |
| Sorbitan sesquioleate | 0.8 |
| Polyoxyethylene oleyl ether (20 E.O.) | 1.2 |
| Compound 1 (Example 2) | 0.5 |
| Perfume | suitable amount |
| Preservative | suitable amount |
| Humectant (propylene glycol) | 5.0 |
| Ethanol | 5.0 |
| Viscous material (1.0% aq. carboxyvinyl polymer) | 20.00 |
| Alkali (potassium hydroxide) | 0.1 |
| Purified Water | Adjusted to 100% |

(3) Cream

TABLE 13

| Ingredients | Incorporation amount (% by weight) |
|---|---|
| Squalane | 5.0 |
| Vaseline | 2.0 |
| Beeswax | 0.5 |
| Sorbitan sesquioleate | 0.8 |
| Polyoxyethyleneoleyl ether (20 E.O.) | 1.2 |
| Perfume | suitable amount |
| Ethyl ester mixture (Example 1) | 1.0 |
| Preservative | suitable amount |
| Humectant (propylene glycol) | 5.0 |
| Ethanol | 5.0 |
| Viscous material (1.0 % aq. carboxyvinyl polymer) | 20.0 |
| Alkali (potassium hydroxide) | 0.1 |
| Purified Water | Adjusted to 100% |

(4) Pack

TABLE 14

| Ingredients | Incorporation amount (% by weight) |
| --- | --- |
| Polyvinyl alcohol | 15.0 |
| Carboxymethylcellulose sodium | 5.0 |
| Propylene glycol | 3.0 |
| Ethanol | 10.0 |
| Perfume Composition | suitable amount |
| Compound 10 (Example 3) | 1.0 |
| Preservative and antioxidant | suitable amount |
| Purified water | Adjusted to 100% |

(5) Bath additive (granular type)

TABLE 15

| Ingredients | Incorporation amount (% by weight) |
| --- | --- |
| Sodium sulfate | 45.0 |
| Sodium bicarbonate | 51.5 |
| Borax | 2.0 |
| Carboxymethylcellulose sodium | 1.0 |
| Pigments | suitable amount |
| Perfume | suitable amount |
| Compound 4 (Example 2) | 0.5 |

(6) Cream foundation

TABLE 16

| Ingredients | Incorporation amount (% by weight) |
| --- | --- |
| Stearic Acid | 5.0 |
| Lipophilic glycerin monostearate | 2.5 |
| Cetostearyl alcohol | 1.0 |
| Propylene glycol monolaurate | 3.0 |
| Fluidic paraffin | 7.0 |
| Isopropyl myristate | 8.0 |
| Butyl paraoxybenzoate | suitable amount |
| Triethanolamine | 1.2 |
| Sorbit | 3.0 |
| Methyl p-oxybenzoate | suitable amount |
| Titanium oxide | 8.0 |
| Kaolin | 5.0 |
| Talk | 2.0 |
| Bentonite | 1.0 |
| Coloring pigment | suitable amount |
| Acid mixture (Example 1) | 1.0 |
| Purified Water | Adjusted to 100% |

According to the present invention, it was revealed that purified products of extracts from specific plants have excellent inhibitory activity on production of melanin, cell-activating activity, and anti-bacterial activity. The melanin inhibitor consisting of this purified product is excellent not only as a skin whitening agent for preventing the formation of stains and freckles, as well as deposition of pigment in the skin after sunburn and for improving appearances, but also superior in safety and product stability. Further, this purified product can be used as an agent for external application onto the skin, which is effective for prevention and treatment of body odors, dandruff, wounds, etc. by activating skin cells themselves and activating the functions of the skin itself to improve skin conditions. These biologically active substances can be incorporated into base cosmetics such as cream, lotion, milky lotion, pack, etc., make-up cosmetics such as foundation, etc., bath additive, agent for external application onto the skin, oral cavity composition (e.g., toothpaste, mouthwash), etc.

What is claimed is:

1. A composition for inhibiting melanin formation consisting essentially of a melanin production inhibiting amount of 0.01 to 10% by weight of a compound represented by formula (1)

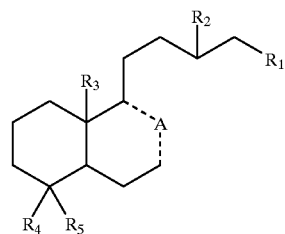

where $R^1$ is —COOR$^6$ or —COOX, where X is a group capable of forming a salt, $R^6$ is hydrogen or $C_1$ to $C_3$ lower alkyl and $R^2$ to $R^5$ each represent hydrogen or methyl; and . . . A . . . is =C(CH$_3$)—, —C(CH$_3$)=, —C(=CH$_2$)—, —CH(CH$_3$)— or —C(OH) (CH$_3$)—; for external application to the skin.

2. The composition of claim 1 further including one or more skin agent selected from the group consisting of arbutin, kojic acid, ellagic acid, ascorbic acid and derivatives thereof.

3. A method of inhibiting melanin production in a human requiring such inhibition comprising applying to the skin of the human a melanin producing inhibiting amount of a compound represented by formula (1)

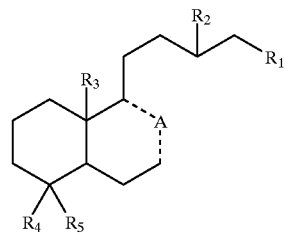

where $R^1$ is —COOR$^6$ or —COOX, where X is a group capable of forming a salt, $R^6$ is hydrogen or $C_1$ to $C_3$ lower alkyl and $R^2$ to $R^5$ each represent hydrogen or methyl; and . . . A . . . is =C(CH$_3$)—, —C(CH$_3$)=, —C(=CH$_2$)—, —CH(CH$_3$)— or —C(OH) (CH$_3$)—.

4. The composition of claim 1, wherein the compound of formula (1) is selected from the group consisting of labdanolic acid, labd-7-en-15-oic acid, labd-8(17)-en-15-oic acid, labd-8-en-15-oic acid and salts and methyl and ethyl esters thereof.

5. The composition of claim 2, wherein the compound of formula (1) is selected from the group consisting of labdanolic acid, labd-7-en-15-oic acid, labd-8(17)-en-15-oic acid, labd-8-en-15-oic acid and salts and methyl and ethyl esters thereof.

6. The method of claim 3, wherein the compound of formula (1) is selected from the group consisting of labdanolic acid, labd-7-en-15-oic acid, labd-8(17)-en-15-oic acid, labd-8-en-15-oic acid and salts and methyl and ethyl esters thereof.

* * * * *